(12) United States Patent
Hosoi et al.

(10) Patent No.: US 10,882,809 B2
(45) Date of Patent: *Jan. 5, 2021

(54) PRODUCTION METHOD FOR HALOGENATED ALPHA-FLUOROETHERS

(71) Applicant: Central Glass Company, Limited, Ube (JP)

(72) Inventors: Kenji Hosoi, Kawagoe (JP); Naoya Ueshima, Kawagoe (JP)

(73) Assignee: Central Glass Company, Limited, Ube (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/474,112

(22) PCT Filed: Dec. 15, 2017

(86) PCT No.: PCT/JP2017/045082
§ 371 (c)(1),
(2) Date: Jun. 27, 2019

(87) PCT Pub. No.: WO2018/123648
PCT Pub. Date: Jul. 5, 2018

(65) Prior Publication Data

US 2019/0352246 A1 Nov. 21, 2019

(30) Foreign Application Priority Data

Dec. 29, 2016 (JP) ................ 2016-257221

(51) Int. Cl.
*C07C 41/22* (2006.01)

(52) U.S. Cl.
CPC .................... *C07C 41/22* (2013.01)

(58) Field of Classification Search
CPC .................... C07C 41/22
See application file for complete search history.

(56) References Cited

U.S. PATENT DOCUMENTS

| | | | |
|---|---|---|---|
| 3,017,436 A | 1/1962 | Hamilton | |
| 3,897,502 A | 7/1975 | Russell et al. | |
| 3,981,927 A | 9/1976 | Siegemund et al. | |
| 4,579,976 A | 4/1986 | Cheminal et al. | |
| 4,762,856 A | 8/1988 | Terrell | |
| 4,874,901 A | 10/1989 | Halpern et al. | |
| 4,972,040 A | 11/1990 | Robin et al. | |
| 5,015,781 A | 5/1991 | Robin et al. | |
| 5,026,924 A | 6/1991 | Cicco | |
| 5,185,474 A | 2/1993 | O'Neill | |
| 5,196,600 A | 3/1993 | O'Neill | |
| 5,205,914 A | 4/1993 | Rozov et al. | |
| 5,278,342 A | 1/1994 | O'Neill et al. | |
| 5,446,211 A | 8/1995 | O'Neill et al. | |
| 5,504,263 A | 4/1996 | Burgess et al. | |
| 5,543,055 A | 8/1996 | O'Neill et al. | |
| 5,696,308 A | 12/1997 | Burgess et al. | |
| 5,750,807 A | 5/1998 | Burgess et al. | |
| 6,054,626 A | 4/2000 | Chambers et al. | |
| 6,225,511 B1 | 5/2001 | Chambers et al. | |
| 6,800,786 B1 | 10/2004 | Rozov et al. | |
| 10,683,252 B2* | 6/2020 | Hosoi ............... | C07C 41/01 |
| 2003/0209685 A1 | 11/2003 | Robin et al. | |
| 2008/0125589 A1 | 5/2008 | Ishii et al. | |
| 2008/0132731 A1 | 6/2008 | Swinson et al. | |
| 2010/0185020 A1 | 7/2010 | Hariharan et al. | |
| 2010/0249302 A1 | 9/2010 | Sugiura et al. | |
| 2011/0082313 A1 | 4/2011 | Ishii et al. | |

FOREIGN PATENT DOCUMENTS

| | | |
|---|---|---|
| DE | 23 61 058 A1 | 6/1975 |
| DE | 26 56 545 A1 | 6/1978 |
| JP | 50-076007 A | 6/1975 |
| JP | 2-104545 A | 4/1990 |
| JP | 2-279646 A | 11/1990 |
| JP | 4-273839 A | 9/1992 |
| JP | 6-87777 A | 3/1994 |

(Continued)

OTHER PUBLICATIONS

International Search Report (PCT/ISA/210) issued in PCT Application No. PCT/JP2017/045083 dated Jan. 23, 2018 with English translation (four (4) pages).

Japanese-language Written Opinion (PCT/ISA/237) issued in PCT Application No. PCT/JP2017/045083 dated Jan. 23, 2018 (three (3) pages).

Fenneteau et al., "Liebeskind-Srogl Cross-Coupling on y-carbozyl-y-butyrolactone Derivatives: Application to the Side Chain of Amphidinolides C and F", Tetrahedron Letters, 2015, pp. 3758-3761, vol. 56, (four (4) pages).

(Continued)

*Primary Examiner* — Rosalynd A Keys

(74) *Attorney, Agent, or Firm* — Crowell & Moring LLP

(57) ABSTRACT

A halogenated α-fluoroether of the formula (2) (where HaloR represents haloalkyl; $R^1$ represents hydrogen, halogen, alkyl or substituted alkyl; and $R^2$ represents alkyl or substituted alkyl) is produced efficiently on an industrial scale by reacting a halogenated aldehyde of the formula (1) (where HaloR represents haloalkyl) or an equivalent thereof with hydrogen fluoride.

$$\text{HaloR} \overset{\text{O}}{-\!\!\!-\!\!\!-} \text{H} \quad (1)$$

$$\text{HaloR} \overset{\text{F}}{\underset{R^1}{-\!\!\!\!\!\!|\!\!\!-}} \text{OR}^2 \quad (2)$$

3 Claims, No Drawings

(56) References Cited

FOREIGN PATENT DOCUMENTS

| | | |
|---|---|---|
| JP | 6-192154 A | 7/1994 |
| JP | 6-298693 A | 10/1994 |
| JP | 7-502037 A | 3/1995 |
| JP | 7-291881 A | 11/1995 |
| JP | 11-506742 A | 6/1999 |
| JP | 2006-290870 A | 10/2006 |
| JP | 2008-150385 A | 7/2008 |
| JP | 2009-286731 A | 12/2009 |
| JP | 2010-533211 A | 10/2010 |
| JP | 2010-254678 A | 11/2010 |
| WO | WO 2006/076324 A2 | 7/2006 |

OTHER PUBLICATIONS

Siegemund, "Darstellung von Trifluoracetaldehyd-alkylhalbacetalen und deren Umwandlung in (2,2,2,-Trifluor-1-halogenaethyl)alkylaether", Chem. Ber., 1973, pp. 2960-2968, (nine (9) pages).

International Search Report (PCT/ISA/210) issued in PCT Application No. PCT/JP2017/045082 dated Jan. 16, 2018 with English translation (four (4) pages).

Japanese-language Written Opinion (PCT/ISA/237) issued in PCT Application No. PCT/JP2017/045082 dated Jan. 16, 2018 (three (3) pages).

Ishii et al., "Trifluoroacetaldehyde", Journal of Synthetic Organic Chemistry, 1999, pp. 102-103, vol. 57, No. 10, with English abstract (four (4) pages).

Bagnall et al., "New Inhalation Anesthetics: Ill Fluorinated Aliphatic Ethers", Journal of Fluorine Chemistry, 1979, pp. 123-140, vol. 13, (18 pages).

Notice of Allowance issued in U.S. Appl. No. 16/474,136 dated Apr. 13, 2020 (12 pages).

\* cited by examiner

PRODUCTION METHOD FOR HALOGENATED ALPHA-FLUOROETHERS

FIELD OF THE INVENTION

The present invention relates to a method for producing a halogenated α-fluoroether.

BACKGROUND ART

Halogenated α-fluoroethers, which are the target compound of the present invention, are important as pharmaceutical and agrichemical intermediates and as chlorofluorocarbon substitutes. In particular, α,β,β,β-tetrafluoroethers are intermediates for production of desflurane as an inhalation anesthetic. As conventional techniques for production of α-fluoroethers, there are known the following methods: a method of reacting a hemiacetal as an equivalent of fluoral (2,2,2-trifluoroacetaldehyde) with a Yarovenko reagent (see Patent Document 1); a method of converting a hemiacetal to a corresponding p-toluenesulfonic acid ester and then fluorinating the ester under basic conditions (see Patent Document 2); a method of adding methanol to hexafluoropropene oxide, thereby forming an ester, followed by decarboxylating the ester (see Patent Document 3); and a method of converting a hemiacetal to a corresponding fluorosulfuric acid ester and then reacting the ester with a "salt or complex of an organic base and hydrogen fluoride" under basic conditions (see Patent Document 4). There has not been known a method of converting a halogenated hemiacetal or halogenated aldehyde to a corresponding halogenated α-fluoroether by fluorination reaction with hydrogen fluoride as in the present invention.

PRIOR ART DOCUMENTS

Patent Documents

Patent Document 1: Japanese Laid-Open Patent Publication No. S50-076007
Patent Document 2: Japanese Laid-Open Patent Publication No. H2-104545
Patent Document 3: Japanese Laid-Open Patent Publication No. H6-088777
Patent Document 4: Japanese Laid-Open Patent Publication No. 2009-286731

SUMMARY OF THE INVENTION

The conventionally known methods for production of halogenated α-fluoroethers are advantageous in small-scale systems. However, many of these conventionally known methods use reagents high in boiling point and difficult to handle and thus require equipment for high-pressure reaction. Further, the conventionally known methods each require complicated separation operation such as precision distillation for isolation of the halogenated α-fluoroether as the target product because the reaction takes place with the use of an organic solvent.

The method of Patent Document 1 uses the Yarovenko reagent as a dehydroxyfluorination agent. This reagent needs to be prepared in advance from chlorotrifluoroethylene, which is low in boiling point, and diethylamine. Moreover, the method of Patent Document 1 is accompanied by stoichiometric generation of a fluorine-containing organic waste as a by-product. It is hence difficult to industrially implement the method of Patent Document 1. The method of Patent Document 2 or 3 goes through two reaction steps, which results in complication of operations including post-treatment so that high productivity cannot be expected. In addition, the method of Patent Document 2 or 3 does not give a satisfactory overall yield. The method of Patent Document 4 needs to use an excessive amount of sulfuryl fluoride, which is low in boiling point, and thus requires a very low reaction temperature (−78° C.), which causes a large load on production equipment. It is hence somewhat difficult to industrially implement the method of Patent Document 4.

Under these circumstances, there has been a strong demand to develop a method for efficiently producing a halogenated α-fluoroether at low cost.

Means for Solving the Problems

The present inventors have made extensive researches in view of the above problems. As a result of the researches, the present inventors have found that a halogenated α-fluoroether of the formula [2] is easily produced by reacting, with hydrogen fluoride, a halogenated aldehyde of the formula [4] or a halogenated hemiacetal of the formula [1] which is an equivalent of the halogenated aldehyde.

[4]

In the formula [4], HaloR represents a haloalkyl group.

[1]

In the formula [1], HaloR represents a haloalkyl group; $R^1$ represents a hydrogen atom, a halogen atom, an alkyl group or a substituted alkyl group; and $R^2$ represents an alky group or a substituted alkyl group.

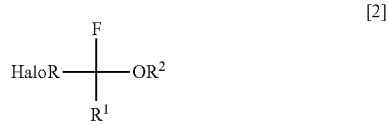
[2]

In the formula [2], HaloR represents a haloalkyl group; $R^1$ represents a hydrogen atom, a halogen atom, an alkyl group or a substituted alkyl group; and $R^2$ represents an alky group or a substituted alkyl group.

In the case of fluorinating the halogenated hemiacetal with hydrogen fluoride, the hydrogen fluoride not only functions as a fluorination agent, but also as an acidic substance because of its acidic nature. There has thus been a concern that, in addition to the fluorination, the halogenated hemiacetal may undergo a side reaction to decompose into a corresponding aldehyde and alcohol. As a result of practical experiments, however, it has been surprisingly found that the fluorination of a hydroxyl group of the halogenated hemiacetal proceeds selectively to form a corresponding halogenated α-fluoroether.

Further, it has been favorably found that the reaction rate of the fluorination is dramatically improved under the coexistence of an orthoester in the reaction system, whereby the halogenated α-fluoroether can be formed with a significantly high yield. The reason for this is assumed to be that the orthoester functions as a dehydration agent to collect water generated during the progress of the fluorination and thereby facilitate the fluorination.

The thus-formed halogenated α-fluoroether can be purified to a higher purity by a very easy process of washing operation. Accordingly, the present invention is of great utility and importance.

Namely, the present invention provides a production method of a halogenated α-fluoroether as set forth in the following inventive aspects 1 to 4.

[Inventive Aspect 1]

A method for producing a halogenated α-fluoroether of the formula [2], comprising reacting a halogenated aldehyde of the formula [4] or an equivalent thereof with hydrogen fluoride.

[Inventive Aspect 2]

The method according to Inventive Aspect 1, wherein the equivalent of the halogenated aldehyde is a halogenated hemiacetal of the formula [1].

[Inventive Aspect 3]

The method according to Inventive Aspect 1 or 2, wherein the reaction is conducted in the presence of an orthoester of the formula [3].

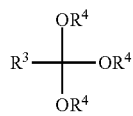

[3]

In the formula [3], $R^3$ represents a hydrogen atom, an alkyl group, a substituted alkyl group or an aryl group; and $R^4$ represents an alkyl group or a substituted alkyl group.

[Inventive Aspect 4]

The method according to any one of Inventive Aspect 1 to 3, wherein the reaction is conducted without the use of an organic solvent.

The present invention achieves the effects of efficiently producing the halogenated α-fluoroether by reaction of the halogenated aldehyde or halogenated hemiacetal with the hydrogen fluoride.

DETAILED DESCRIPTION OF THE EMBODIMENTS

Hereinafter, the present invention will be described in detail below. It should be understood that the present invention is not limited to the following embodiments and can be embodied as appropriate, based on the common knowledge of those skilled in the art, within the range that does not impair the effects of the present invention.

In the halogenated aldehyde of the formula [4] and in the halogenated hemiacetal of the formula [1], HaloR represents a haloalkyl group. Examples of the haloalkyl group are a linear or branched alkyl group of 1 to 6 carbon atoms and a cyclic alkyl group of 3 to 6 carbon atoms, in each of which any number of and any combination of halogen atoms (such as fluorine, chlorine, bromine and iodine) may be substituted onto any of carbon atoms. Above all, the haloalkyl group is preferably of 1 to 4 carbon atoms, more preferably 1 carbon atom.

Further, the haloalkyl group is preferably a fluoroalkyl group in which hydrogen has been substituted with fluorine or a chloroalkyl group in which hydrogen has been substituted with chlorine. Particularly preferred a perfluoroalkyl or perchloroalkyl group in which all of hydrogen atoms have been substituted with fluorine or chlorine.

Specific examples of the haloalkyl group are trifluoromethyl, pentafluoroethyl, heptafluoropropyl, nonafluorobutyl, trichloromethyl, pentachloroethyl, heptachloropropyl and nonachlorobutyl. Among others, trifluoromethyl, pentafluoroethyl, trichloromethyl and pentachloroethyl are preferred. Particularly preferred are trifluoromethyl and trichloromethyl because the halogenated aldehyde with a trifluoromethyl group is low in cost and high in reactivity.

In the halogenated hemiacetal of the formula [1], $R^1$ represents a hydrogen atom, a halogen atom, an alkyl group or a substituted alkyl group. Examples of the halogen atom are fluorine, chlorine, bromine and iodine. Examples of the alkyl group are a linear or branched alkyl group of 1 to 18 carbon atoms and a cyclic alkyl group of 3 to 18 carbon atoms. Examples of the substituted alkyl group are those each obtained by substituting, onto any carbon atom of the above alkyl group, a substituent such as halogen atom, lower alkoxy group, lower haloalkoxy group, cyano group, lower alkoxycarbonyl group, aromatic ring group, carboxyl group, protected carboxyl group, amino group, protected amino group, hydroxyl group, protected hydroxyl group or the like.

As the substituent of the substituted alkyl group, specific examples of the halogen atom are fluorine, chlorine, bromine and iodine; specific examples of the lower alkoxy group are fluoromethoxy, chloromethoxy and bromomethoxy; specific examples of the lower alcoxycarbonyl group are methoxycarbonyl, ethoxycarbonyl and propoxycarbonyl; and specific examples of the aromatic ring group are phenyl, naphthyl, anthryl, pyrrolyl (including nitrogen-protected form), pyridyl, furyl, thienyl, indolyl (including nitrogen-protected form), quinolyl, benzofuryl and benzothienyl. The term "lower" as used herein means that the group to which the term is attached has a linear or branched structure of 1 to 6 carbon atoms or a cyclic structure of 3 to 6 carbon atoms.

Among the alkyl groups, preferred are methyl, ethyl, n-propyl, i-propyl, n-butyl, s-butyl, t-butyl, n-pentyl and n-hexyl. Among the substituted alkyl groups, preferred are fluoromethyl, chloromethyl, bromomethyl, iodomethyl, trifluoroethyl, trichloroethyl, tribromoethyl and triiodoethyl. As $R^1$, hydrogen is particularly preferred because the halogenated hemiacetal having hydrogen as $R^1$ is stable.

In the halogenated hemiacetal of the formula [1], $R^2$ represents an alkyl group or a substituted alkyl group. The definitions of the alkyl and substituted alkyl groups as $R^2$ are the same as those as $R^1$ in the halogenated hemiacetal of the formula [1]. Among others, an alkyl group is preferred. Particularly preferred are methyl and ethyl because the halogenated hemiacetal having methyl or ethyl as $R^2$ is high in reactivity.

Herein, $R^1$ and $R^2$ in the halogenated hemiacetal of the formula [1] can be independently selected from the above-defined groups.

The halogenated hemiacetal of the formula [1] shows a stereochemistry where the carbon atom to which a hydroxyl group is attached is an asymmetric carbon atom, except for the case where HaloR and $R^1$ are of the same kind of substituent group. The halogenated hemiacetal with asymmetric carbon can be used as either a racemic mixture or an optically active substance in the fluorination reaction.

It is feasible to prepare the halogenated aldehyde of the formula [4] and the halogenated hemiacetal of the formula [1] by known methods. For example, the halogenated aldehyde of the formula [4] immediately reacts with an alcohol to form a stable hemiacetal, that is, the halogenated hemiacetal of the formula [1]. More specifically, fluoral (2,2,2-trifluoroacetaldehyde) is converted to a corresponding methyl hemiacetal or ethyl hemiacetal by reaction with methanol or ethanol. In other words, the halogenated hemiacetal can be prepared by reacting the halogenated aldehyde with the alcohol. Since the methyl hemiacetal or ethyl hemiacetal of fluoral is commercially available, it is convenient to utilize such a commercially available hemiacetal. In the present invention, the target halogenated α-fluoroether of the formula [2] is efficiently produced from the halogenated aldehyde of the formula [4] as will be demonstrated in the below Examples.

In the orthoester of the formula [3], $R^3$ represents a hydrogen atom, an alkyl group, a substituted alkyl group or an aryl group. The definitions of the alkyl and substituted alkyl groups as $R^3$ are the same as those as $R^2$ in the halogenated hemiacetal of the formula [1].

Specific examples of the alkyl group as $R^3$ are methyl, ethyl, n-propyl, i-propyl, n-butyl, s-butyl, t-butyl, n-pentyl and n-hexyl. Specific examples of the aryl group as $R^3$ are phenyl, naphthyl, anthryl, pyrrolyl (including nitrogen-protected form), pyridyl, furyl, thienyl, indolyl (including nitrogen-protected form), quinolyl, benzofuryl and benzothienyl.

Among others, hydrogen, methyl, ethyl and propyl are preferred. Particularly preferred are hydrogen, methyl and ethyl because the orthoester having hydrogen, methyl or ethyl as $R^3$ is low in cost.

In the orthoester of the formula [3], $R^4$ represents an alkyl group or a substituted alkyl group. The definitions of the alkyl and substituted alkyl groups as $R^4$ are the same as those as $R^3$ in the orthoester. Herein, $R^4$ and $R^3$ can also be selected independently.

Among the above definitions, alkyl is preferred as $R^4$. Specific example of the alkyl group as $R^4$ are methyl, ethyl, n-propyl, i-propyl, n-butyl, s-butyl, t-butyl, n-pentyl and n-hexyl. Above all, methyl ethyl and propyl are preferred. Particularly preferred are methyl and ethyl because the orthoester having methyl or ethyl as $R^4$ is high in reactivity.

In the present invention, it is a preferable embodiment to add the orthoester of the formula [3] to the reaction system because the conversion rate of the fluorination reaction is improved with the addition of such an orthoester. With the progress of the fluorination reaction between the halogenated aldehyde of the formula [4] or the halogenated hemiacetal of the formula [1] and the hydrogen fluoride, not only the target compound but also water molecule are formed as indicated in the following scheme. It is assumed that the orthoester of the formula [3] functions as a scavenger against the water molecule. Namely, the orthoester of the formula [3] immediately undergoes hydrolysis under acidic conditions due to the presence of the hydrogen fluoride, thereby giving one ester molecule and two alcohol molecules.

In this way, the orthoester reacts with water to form the alcohol (that is, functions as the dehydration agent). The co-produced ester can be easily separated from the target compound (halogenated α-fluoroether of the formula [2]) after the reaction.

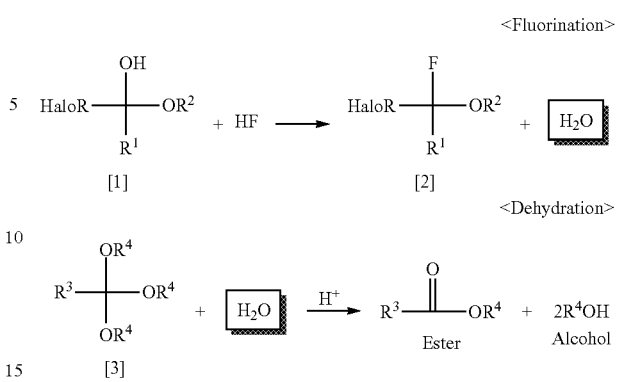

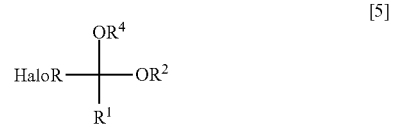

In order for the orthoester of the formula [3] to function as the dehydration agent, the amount of the orthoester used is generally 0.2 equivalent or more, preferably 0.5 to 1.5 equivalents, per 1 equivalent of the halogenated aldehyde of the formula [4] or the halogenated hemiacetal of the formula [1]. When the orthoester of the formula [3] is used in an amount exceeding 1.5 equivalents, the selectivity of formation of the target halogenated α-fluoroether of the formula [2] may be slightly lowered due to the generation of an acetal of the formula [5] as a compound in equilibrium with the halogenated hemiacetal of the formula under the influence of the alcohol ($R^4OH$) by-produced in the dehydration reaction. It is thus preferable to use the orthoester of the formula [3] in the above-specified amount.

[5]

$$HaloR \overset{OR^4}{\underset{R^1}{\rule{1cm}{0.4pt}}} OR^2$$

In the formula [5], HaloR represents haloalkyl; $R^1$ represents hydrogen, halogen, alkyl or substituted alkyl; and $R^2$ represents alkyl or substituted alkyl.

It is expected that a part of the halogenated aldehyde of the formula [4] as the starting raw material would be converted to a hemiacetal under the action of the alcohol generated by decomposition of the orthoester of the formula [3] in the reaction system. It is thus preferable, in the case of using the halogenated aldehyde as the starting material, to add the orthoester to the reaction system for efficient production of the halogenated α-fluoroether in the present invention.

The amount of the hydrogen fluoride used as the fluorination agent is generally 1 equivalent or more per 1 mol of the halogenated hemiacetal of the formula [1] or the halogenated aldehyde of the formula [4]. In order for the reaction to proceed smoothly, the amount of the hydrogen fluoride used is preferably 2 to 10 equivalents per the hemiacetal or aldehyde. In terms of post-treatment, the amount of the hydrogen fluoride used is more preferably 3 to 6 equivalents per the hemiacetal or aldehyde.

The reaction can be conducted with the use of a reaction solvent such as aliphatic hydrocarbon solvent, halogenated hydrocarbon solvent, ether solvent, ester solvent, amide solvent, nitrile solvent or sulfoxide solvent. Specific examples of the reaction solvent are n-hexane, cyclohexane, n-heptane, benzene, toluene, ethylbenzene, xylene, mesitylene, methylene chloride, chloroform, 1,2-dichloroethane, diethyl ether, tetrahydrofuran, diisopropyl ether, tert-butyl methyl ether, ethyl acetate, n-butyl acetate, N,N-dimethylformamide, N,N-dimethylacetamide, N-methylpyrrolidone, 1,3-dimethyl-2-imidazolidinone, acetonitrile, propionitrile and dimethyl sulfoxide. These reaction solvents can be used solely or in combination thereof.

Alternatively, the reaction may be conducted without the use of the reaction solvent. This alternative embodiment is preferred because it is advantageously possible to facilitate purification operation after the reaction and obtain the target compound with high purity only by washing operation as will be demonstrated in the after-mentioned Examples.

The temperature condition of the reaction is generally in the range of −50 to +100° C., preferably −20 to +50° C., more preferably 0 to +20° C.

The pressure condition of the reaction is generally in the range from atmospheric pressure to 0.9 MPa (on the basis of absolute pressure; the same applies to the following), preferably from atmospheric pressure to 0.5 MPa, more preferably from atmospheric pressure to 0.2 MPa.

In the present invention, there can be used a reactor in which the reaction can be sufficiently carried out under atmospheric pressure or pressurized condition. Examples of the reactor are vessels made of metal materials such as stainless steel, Monel™, Hastelloy™, nickel and the like and vessels formed with internal linings of tetrafluoroethylene resin, chlorotrifluoroethylene resin, vinylidene fluoride resin, PFA resin, polypropylene resin, polyethylene resin and the like.

The reaction time is generally 12 hours or less. Since the reaction time varies according to the combination of the starting raw material (formula [1] or [4]) and the orthoester (formula [3]) and the reaction conditions depending on the amount of the hydrogen fluoride used, it is preferable to determine the time at which almost all of the starting raw material has disappeared as the end of the reaction while monitoring the progress of the reaction by any analytical means such as gas chromatography, thin-layer chromatography, liquid chromatography or nuclear magnetic resonance.

The target halogenated α-fluoroether of the general formula [2] is readily obtained by performing ordinary purification operation as post-treatment on the reaction-terminated liquid. The target compound can be purified to a higher chemical purity as required by treatment with activated carbon, distillation, recrystallization, column chromatography or the like.

EXAMPLES

The present invention will be described in more detail below by way of the following examples. It should be understood that the following examples are not intended to limit the present invention thereto.

Example 1

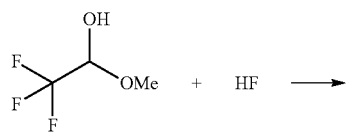

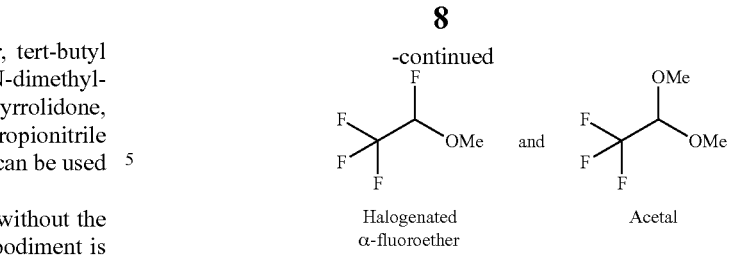

Halogenated α-fluoroether and Acetal

In a 100-mL pressure-proof reaction vessel made of stainless steel (SUS) and equipped with a pressure gauge, a stirrer made of polytetrafluoroethylene (PTFE) was placed. Then, 5.0 g (38.4 mmol) of halogenated hemiacetal shown in the above scheme and 3.8 g (192.2 mmol) of hydrogen fluoride were weighed and put into the reaction vessel under ice cooling. After the temperature of the reaction vessel was naturally raised, the resulting liquid was reacted with stirring for 2 hours at room temperature. After the reaction, the internal vessel pressure of 0.15 MPa was released. The thus-obtained reaction liquid was sampled. Anhydrous calcium chloride was added to the liquid sample to remove unreacted hydrogen fluoride therefrom by absorption. After that, the liquid sample was analyzed by $^{19}$F-NMR. It was confirmed that halogenated α-fluoroether shown in the above scheme was obtained with a conversion rate of 29.2% and a selectivity of 93.5%. The by-product rate of acetal shown in the above scheme was 3.7%.

[Property Data]

1,2,2,2-Tetrafluoroethyl methyl ether $^{1}$H-NMR (400 MHz, CDCl$_3$) δ (ppm): 3.72 (3H, s), 5.28 (1H, dq, J=60.0, 3.2 Hz).

$^{19}$F-NMR (400 MHz, CDCl$_3$, CFCl$_3$) δ (ppm): −84.33 (3F, s), −146.04 (1F, d, J=60.7 Hz).

Example 2

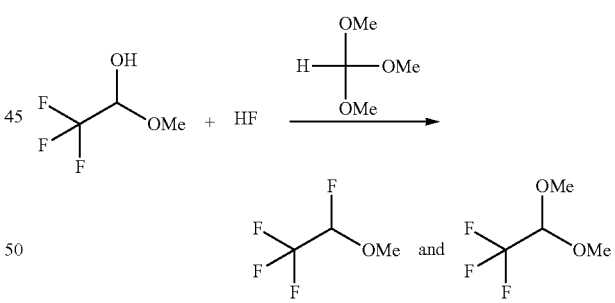

In a 100-mL pressure-proof reaction vessel made of stainless steel (SUS) and equipped with a pressure gauge, a stirrer made of polytetrafluoroethylene (PTFE) was placed. Then, 5.0 g (38.4 mmol) of halogenated hemiacetal shown in the above scheme, 3.8 g (192.2 mmol) of hydrogen fluoride and 2.0 g (19.2 mmol) of methyl orthoformate were weighed and put into the reaction vessel under ice cooling. After the temperature of the reaction vessel was naturally raised, the resulting liquid was reacted with stirring for 2 hours at room temperature. After the reaction, the internal vessel pressure of about 0.10 MPa was released. The thus-obtained reaction liquid was analyzed by $^{19}$F-NMR. It was confirmed that halogenated α-fluoroether shown in the above scheme was obtained with a conversion rate of 54.0% and a selectivity of 93.4%. The by-product rate of acetal shown in the above scheme was 2.4%.

Examples 3 and 4

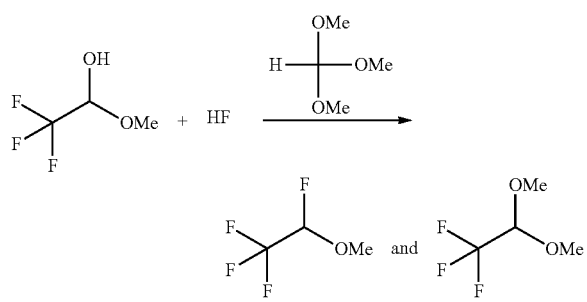

In each of Examples 3 and 4, the reaction was conducted under the same conditions as in Example 2, except that the amount of the methyl orthoformate added was varied. The results of the Examples 3 and 4 are shown together with the results of Examples 1 and 2 in TABLE 1. The analysis conditions in these examples were the same as those in Example 2.

TABLE 1

| Example | Methyl orthoformate (equivalent) | Conversion rate (%) | Selectivity (%) | Dimethyl acetal (%) |
| --- | --- | --- | --- | --- |
| 1 | None | 29.2 | 93.5 | 3.7 |
| 2 | 0.5 | 54.0 | 93.4 | 2.4 |
| 3 | 1 | 78.8 | 92.0 | 4.8 |
| 4 | 1.5 | 71.5 | 85.0 | 12.7 |

As is seen from the above results, the halogenated α-fluoroether was obtained with high selectivity in each Example. Further, it was confirmed that the rate of conversion of the starting raw material was improved with the addition of methyl orthoformate.

Example 5

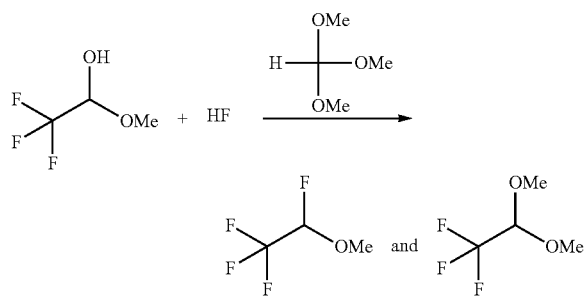

In a 250-ml reaction vessel made of tetrafluoroethylene-perfluoroalkyl vinyl ether copolymer (PFA) and equipped with a thermometer, a stirrer made of polytetrafluoroethylene (PTFE) was placed. Then, 50.0 g (384 mmol) of halogenated hemiacetal shown in the above scheme was weighed and put into the reaction vessel. The reaction vessel was cooled. After that, 38.4 g (1.92 mol) of hydrogen fluoride was introduced into the reaction vessel at an internal vessel temperature of −2.0 to 15.9° C. Subsequently, 40.8 g (384 mmol) of methyl orthoformate was introduced by a metering pump into the reaction vessel at an internal vessel temperature of −1.8 to 29.8° C. After the temperature of the reaction vessel was naturally raised, the resulting liquid was reacted for 2 hours at room temperature. The thus-obtained reaction liquid was analyzed by $^{19}$F-NMR. It was confirmed that: halogenated α-fluoroether shown in the above scheme was obtained with a conversion rate of 78.4% and a selectivity of 90.9%; and acetal shown in the above scheme was obtained as a by-product at a rate of 4.4%. After the reaction, the reaction liquid was cooled again. The reaction was terminated by adding 80 g of ion-exchanged water to the reaction liquid with caution against heat generation. The reaction liquid was washed with water for 10 minutes and subjected to two-layer separation. There was thus obtained 37.2 g of the organic layer with a GC purity of 68.6%. Since methyl formate and methanol as products of hydrolysis of the methyl orthoformate were contained in the organic layer, the organic layer was washed with 80 g of 16% potassium hydroxide solution. By this washing operation, 25.1 g of the halogenated α-fluoroether was obtained with a GC purity of 87.1% and a yield of 49.5%.

Example 6

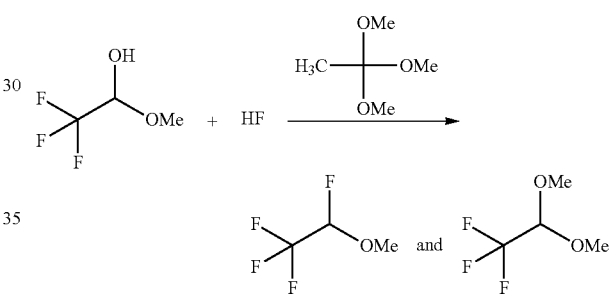

In a 100-mL pressure-proof reaction vessel made of stainless steel (SUS) and equipped with a pressure gauge, a stirrer made of polytetrafluoroethylene (PTFE) was placed. Then, 5.0 g (38.4 mmol) of halogenated hemiacetal shown in the above scheme, 3.8 g (192.2 mmol) of hydrogen fluoride and 4.6 g (38.4 mmol) of methyl orthoformate were weighed and put into the reaction vessel under ice cooling. After the temperature of the reaction vessel was naturally raised, the resulting liquid was reacted with stirring for 5 hours at room temperature. After the reaction, the internal vessel pressure of about 0.10 MPa was released. The thus-obtained reaction liquid was analyzed by $^{19}$F-NMR. It was confirmed that halogenated α-fluoroether shown in the above scheme was obtained with a conversion rate of 55.9% and a selectivity of 94.1%. The by-product rate of acetal shown in the above scheme was 2.1%.

Example 7

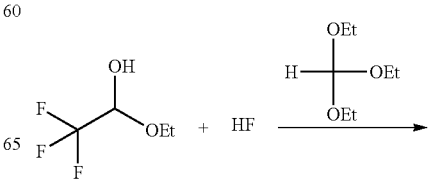

-continued

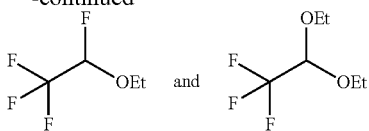

In a 100-mL pressure-proof reaction vessel made of stainless steel (SUS) and equipped with a pressure gauge, a stirrer made of polytetrafluoroethylene (PTFE) was placed. Then, 5.0 g (34.7 mmol) of halogenated hemiacetal shown in the above scheme, 3.5 g (173.6 mmol) of hydrogen fluoride and 5.1 g (34.7 mmol) of ethyl orthoformate were weighed and put into the reaction vessel under ice cooling. After the temperature of the reaction vessel was naturally raised, the resulting liquid was reacted with stirring for 5 hours at room temperature. After the reaction, the internal vessel pressure of about 0.1 MPa was released.

The thus-obtained reaction liquid was analyzed by $^{19}$F-NMR. It was confirmed that halogenated α-fluoroether was obtained with a conversion rate of 69.3% and a selectivity of 93.7%. The by-product rate of acetal shown in the above scheme was 4.4%.

[Property Data]

1,2,2,2-Tetrafluoroethyl ethyl ether $^1$H-NMR (400 MHz, CDCl$_3$) δ (ppm): 1.33 (3H, t, J=7.1 Hz), 3.83 (1H, m), 4.03 (1H, m), 5.36 (1H, dq, J=61.8, 3.2 Hz).
$^{19}$F-NMR (400 MHz, CDCl$_3$, CFCl$_3$) δ (ppm): −84.36 (3F, s), −142.60 (1F, d, J=60.7 Hz).

Example 8

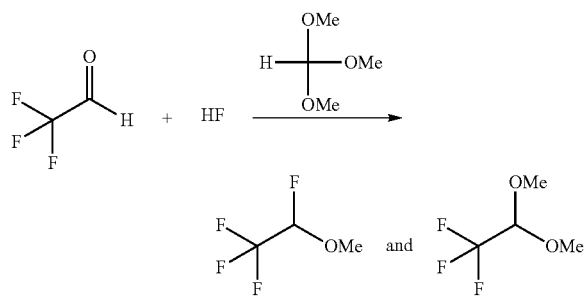

In a 250-ml reaction vessel made of tetrafluoroethylene-perfluoroalkyl vinyl ether copolymer (PFA) and equipped with a thermometer, a stirrer made of polytetrafluoroethylene (PTFE) was placed. Then, 44.4 g (2.22 mmol) of hydrogen fluoride was put into the reaction vessel; and 54.5 g (555 mmol) of fluoral, which was separately formed by a known method (as disclosed in Journal of Synthetic Organic Chemistry (Japan), 1999, vol. 57, no. 10, p. 102-103), was poured into the hydrogen fluoride at an internal vessel temperature of −1.1 to 21.0° C. After that, 50.1 g (472 mmol) of methyl orthoformate was dropped into the reaction vessel at an internal vessel temperature of −5 to 25.5° C. The resulting liquid was reacted for 1 hour at room temperature and then cooled again. The reaction was terminated by adding 90 g of ion-exchanged water to the reaction liquid with caution against heat generation. The reaction liquid was washed with water for 10 minutes and subjected to two-layer separation. There was thus obtained 51.8 g of the organic layer with a GC purity of 75.7%. Since methyl formate and methanol as products of hydrolysis of the methyl orthoformate were contained in the organic layer, the organic layer was washed with 90 g of 16% potassium hydroxide solution. By this washing operation, 39.1 g of halogenated α-fluoroether was obtained with a GC purity of 97.6% and a yield of 53.3%.

Example 9

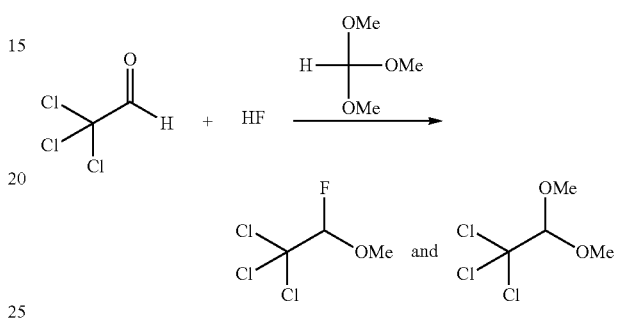

Into a 1000-mL pressure-proof reaction vessel made of stainless steel (SUS) and equipped with a thermometer and a stirring motor, 162 g (8.14 mol) of hydrogen fluoride and 400 g (2.71 mol) of chloral were weighed and put. Under cooling, 288 g (2.71 mol) of methyl orthoformate was dropped into the reaction vessel at an internal vessel temperature of 4.0 to 26.7° C. The resulting liquid was reacted for 1 hour at room temperature and then cooled again. The reaction was terminated by adding 400 g of ion-exchanged water to the reaction liquid with caution against heat generation. The reaction liquid was washed with water for 10 minutes and subjected to two-layer separation. There was thus obtained 555 g of the organic layer with a GC purity of 77.1%. Since methyl formate and methanol as products of hydrolysis of the methyl orthoformate were contained in the organic layer, the organic layer was washed with 600 g of 16% potassium hydroxide solution. By this washing operation, 443 g of halogenated α-fluoroether was obtained with a GC purity of 94.2% and a yield of 90.0%.

[Property Data]

1-Fluoro-2,2,2-trichloroethyl methyl ether $^1$H-NMR (400 MHz, CDCl$_3$) δ (ppm): 3.75 (3H, d, J=1.58 Hz), 5.34 (1H, d, J=63.8 Hz).
$^{19}$F-NMR (400 MHz, CDCl$_3$, CFCl$_3$) δ (ppm): −128.1 (1F, d, J=63.7 Hz).

INDUSTRIAL APPLICABILITY

The target halogenated α-fluoroether of the present invention, particularly α,β,β,β-tetrafluoroether, is useful as an intermediate for production of inhalation anesthetic desflurane.

The invention claimed is:
1. A method for producing a halogenated α-fluoroether of the formula [2], comprising reacting a halogenated aldehyde of the formula [4] or an equivalent thereof with hydrogen fluoride

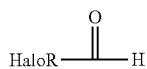

[4]

where HaloR represents a haloalkyl group

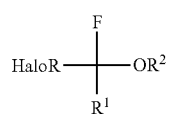

[2]

where HaloR represents a haloalkyl group; $R^1$ represents a hydrogen atom, a halogen atom, an alkyl group or a substituted alkyl group; and $R^2$ represents an alkyl group or a substituted alkyl group,
wherein the reacting is conducted in the presence of an orthoester of the formula [3]

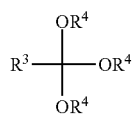

[3]

where $R^3$ represents a hydrogen atom, an alkyl group, a substituted alkyl group or an aryl group; and $R^4$ represents an alkyl group or a substituted alkyl group.

2. The method according to claim 1, wherein the equivalent of the halogenated aldehyde is a halogenated hemiacetal of the formula [1]

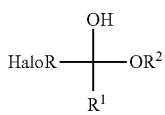

[1]

where HaloR represents a haloalkyl group; $R^1$ represents a hydrogen atom, a halogen atom, an alkyl group or a substituted alkyl group; and $R^2$ represents an alkyl group or a substituted alkyl group.

3. The method according to claim 1, wherein the reacting is conducted without the use of an organic solvent.

* * * * *